United States Patent [19]

Schmiesing et al.

[11] Patent Number: 5,334,720
[45] Date of Patent: Aug. 2, 1994

[54] DIPHENYL-1-(AMINOALKYL)-2-PIPERIDINONE AND -2-PYRROLIDINONE DERIVATIVES HAVING ANTICONVULSANT PROPERTIES

[75] Inventors: Richard J. Schmiesing, Pittsford; Robert J. Murray, Rochester, both of N.Y.

[73] Assignee: Fisons Corporation, Rochester, N.Y.

[21] Appl. No.: 666,120

[22] Filed: Mar. 7, 1991

[51] Int. Cl.$^5$ .......................................... C07D 401/00
[52] U.S. Cl. .................... 546/208; 546/217; 546/245; 548/524; 548/541
[58] Field of Search ...................... 546/245, 708, 717; 548/546, 524

[56] References Cited

U.S. PATENT DOCUMENTS

| | | | |
|---|---|---|---|
| 2,742,475 | 4/1956 | Hoffmann et al. | 260/293.4 |
| 3,468,893 | 9/1969 | Mizzoni et al. | 260/293 |
| 3,718,743 | 2/1973 | Shen et al. | 424/267 |
| 4,216,221 | 8/1980 | Lannoy | 424/274 |

FOREIGN PATENT DOCUMENTS 47-42656 12/1972 Japan .

OTHER PUBLICATIONS

Utjes-Le Gall et al., Bull. Soc. Chim. Fr. No. 11-12, 1175-1181 (1977) Synthèse et étude d'ω-amino-acides.
Yamawaki et al., Y Zasshi, 97 (2), 127-134 (1977). Studies on Synthetic Drugs I.
Yamawaki et al., Chem. Abs. 78 84269r (Abstracting Japan Kokai 47/42656) 5,5-Diphenyl-2-pyrrolidone and 6,6-diphenyl-2-piperidinone derivatives (Dec. 1972).

Primary Examiner—C. Warren Ivy
Assistant Examiner—Raymond Covington
Attorney, Agent, or Firm—McAulay Fisher Nissen Goldberg & Kiel

[57] ABSTRACT

Compounds of the formula I,

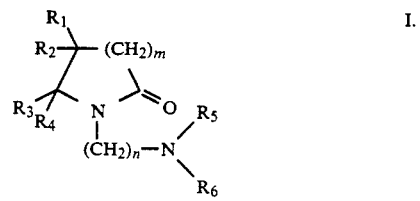

wherein
$R_1$, $R_2$, $R_3$ and $R_4$ independently represent hydrogen, alkyl, phenyl or substituted phenyl with the proviso that two of $R_1$, $R_2$, $R_3$ or $R_4$ are phenyl or substituted phenyl and two of $R_1$, $R_2$, $R_3$ or $R_4$ are hydrogen or alkyl;
m represents an integer from 1-2; and
n represents an integer from 1-3;

or a pharmaceutically acceptable salt thereof. The compounds are useful as pharmaceuticals, in particular, in the treatment of epilepsy.

4 Claims, No Drawings

DIPHENYL-1-(AMINOALKYL)-2-PIPERIDINONE AND -2-PYRROLIDINONE DERIVATIVES HAVING ANTICONVULSANT PROPERTIES

SUMMARY

This invention relates to novel diphenyl-1-(aminoalkyl)-2-piperidinone and -2-pyrrolidinone derivatives, processes for their preparation, pharmaceutical formulations containing them and their biological properties.

BACKGROUND

Compounds of the invention possess useful pharmaceutical properties. In particular they possess anticonvulsant properties and thus are useful in the treatment of epilepsy.

U.S. Patent 4,216,221 discloses 1-(aminoalkyl)-2-piperidinones and -2-pyrrolidinones as intermediates for 1,3-disubstituted-2-thioureas with pharmaceutical properties.

DETAILED DESCRIPTION

According to this invention we provide novel compounds of the formula I,

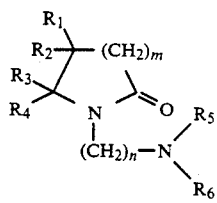

wherein, $R_1$, $R_2$, $R_3$ and $R_4$, which may be the same or different independently represent hydrogen, $C_{1-6}$ alkyl, phenyl or phenyl substituted by one or more halogen, hydroxyl, nitro, amino, $C_{1-6}$ alkyl or $C_1$-$C_6$ alkoxy groups;

$R_5$ and $R_6$ independently represent hydrogen, $C_1$-$C_6$ alkyl or $C_3$-$C_6$ cycloalkyl, or $R_5$ and $R_6$ together with the nitrogen form a $C_{4-6}N$ heterocycle;

m represents an integer from 1–2; and n represents an integer from 1–3;

provided that, two of the substituents $R_1$, $R_2$, $R_3$ and $R_4$ independently represent phenyl or substituted phenyl and the other two independently represent hydrogen or $C_{1-6}$alkyl;

or a pharmaceutically acceptable acid addition salt thereof.

Pharmaceutically acceptable acid addition salts of the compounds of formula I include salts of mineral acids, for example, hydrohalic acids, e.g. hydrochloric or hydrobromic; or organic acids, e.g. formic, acetic or lactic acids. The acid may be polybasic, for example sulphuric, fumaric, maleic or citric acid.

This invention also relates to all stereoisomeric forms and optical enantiomeric forms of the compounds of formula I.

According to the invention there is also provided a process for the preparation of compounds of formula I or pharmaceutically acceptable acid addition salts or solvates thereof, which comprises, a) preparing a compound of formula I by reacting a corresponding compound of formula II,

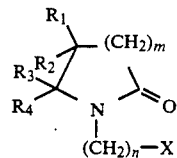

wherein X is a suitable leaving group with a corresponding amine of the formula $R_5R_6NH$, or b) preparing a compound of formula I in which n is 2 or by reacting a corresponding compound of formula III,

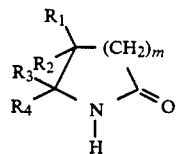

with a corresponding compound of formula IV,

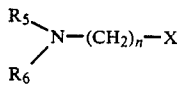

wherein X is a suitable leaving group and $R_5$ or $R_6$ are as defined above or optionally may constitute a protecting group, or c) preparing a compound of formula I containing one or more amino or hydroxyl groups by removing a protecting group from a compound of formula I in which one or more of the amino or hydroxyl groups is protected, and where desired or necessary converting the resulting compound of formula I into a pharmaceutically acceptable acid addition salt thereof or vice versa.

In the reaction of process (a) suitable leaving groups X are represented by, for example, halogen, preferably chlorine, bromine or iodine, or an alkyl- or arylsulfonate group for example methanesulfonate or p-toluenesulfonate. The amination reaction may be carried out in a suitable inert solvent, for example an aprotic solvent such as toluene or tetrahydrofuran and at a temperature of, for example from $-80°$–$120°$ C.

In the reaction of process (b), in which the leaving group X may be the same as in process (a), the alkylation reaction may be carried out in the presence of a base, for example, an alkali hydroxide such as potassium hydroxide in a polar solvent, for example, dimethylsulfoxide, ethanol or water or mixtures thereof. Suitable protecting groups that $R_5$ and $R_6$ may together constitute include: a urethane protecting group such as benzyloxycarbonyl (CBZ) or t-butyloxycarbonyl (BOC); or $R_5$ and $R_6$ together with the nitrogen atom to which they are attached may form a phthalimide group.

In process (c) the amine protecting groups may be removed by either catalytic hydrogenation for the CBZ group, a suitable catalyst being palladium or platinum on carbon, and the reaction being suitably carried out in an inert solvent such as methanol; treatment with an acid such as trifluoracetic or hydrochloric acid for the BOC group; or treatment with hydrazine in a lower alkanol such as ethanol for the phthalimide group.

Acid addition salts of compounds of formula I may be formed by reacting the free base, or a salt or derivative thereof with one or more equivalents of the appropriate acid. The reaction may be carried out in a solvent in which the salt is insoluble or in which the salt is soluble or in mixtures of the solvents. Acid addition salts may be converted to the free base by the action of a stronger base.

The starting materials for reactions (a) to (c) may be prepared by a number of methods, for example, d) the compounds of formula II may be prepared by, 1) reacting the corresponding compound of formula III,

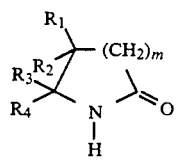

with formaldehyde to give a compound of formula V,

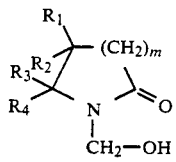

2) reacting the compound of formula V with a halogenating agent or an alkyl- or arylsulfonyl halide to give the corresponding compound of formula II.

The reaction with formaldehyde may be carried out in a suitable solvent, for example, a protic solvent such as aqueous alcoholic media, for example, aqueous ethanol in the presence of a base such as sodium hydroxide, and at a temperature of, for example, from 20°–100° C. The resulting hydroxymethyl derivative may be reacted with, for example, a halogenating reagent such as thionyl chloride, in an inert solvent such as, for example, methylene chloride or benzene. The halogenation reaction may be carried at a temperature of, for example, from 0°–100° C. Alternatively the hydroxy compound may be reacted with an alkyl- or arylsulfonyl halide in the presence of a base, for example, pyridine or triethylamine in a suitably inert solvent such as toluene or tetrahydrofuran, and at a temperature of, for example, from 20°–120° C.

The intermediate compounds of formula III are either well known or may be prepared from compounds known per se by conventional methods according to literature procedures for the known compounds or suitable modifications thereof as described in the examples.

Methods for preparing phenyl and substituted-phenyl 2-pyrrolidinones and 2-piperidinones may be found in: U.S. Pat. Nos. 2,742,475; 3,468,893; 3,718,743; Japanese patent 47/42656;
Utjes-Le Gall et al, Bull. Soc. Chim. Ft. No 11–12, 1175–1181 (1977); and
Y Yamawaki et al, Y. Zasshi, 97 (2), 177 (1977), which are hereby incorporated by reference.

In the compounds of formula I: alkyl groups which $R_1$, $R_2$, $R_3$, $R_4$, $R_5$ and $R_6$ may represent include methyl, ethyl, propyl, isopropyl, n-butyl, iso-butyl and s-butyl;

cycloalkyl groups which $R_5$ and $R_6$ may represent include cyclopropyl, cyclobutyl, cyclopentyl and cyclohexyl;

$C_{1-6}$ alkoxy groups include methoxy, ethoxy and propoxy;

halogen groups include fluorine, chlorine, bromine or iodine;

We prefer compounds of formula I or a pharmaceutically acceptable acid addition salt thereof, in which;

$R_1$ is hydrogen, phenyl or substituted phenyl, preferably phenyl;

$R_2$ is hydrogen, phenyl or substituted phenyl, preferably phenyl;

$R_3$ is hydrogen, phenyl or substituted phenyl, preferably hydrogen;

$R_4$ is hydrogen, phenyl or substituted phenyl, preferably hydrogen;

$R_5$ is hydrogen, $C_{1-3}$alkyl or cyclopropyl, preferably hydrogen or methyl;

$R_6$ is hydrogen, $C_{1-3}$alkyl or cyclopropyl, preferably hydrogen or methyl;

m represents an integer from 1–2 preferably 2;

n represents an integer from 1–2, preferably 1.

We especially prefer compounds of formula I in which $R_1$ and $R_2$ are both phenyl.

We especially prefer compounds of formula I in which one of $R_5$ and $R_6$ is hydrogen and the other is hydrogen or methyl.

The compounds of formula I, and their pharmaceutically acceptable acid addition salts, are useful because they possess pharmacological activity in animals. In particular, the compounds have useful anti-epileptic properties as demonstrated by their ability to inhibit maximal electroshock (MES) induced seizures in mice. Antiepileptic activity may be measured by assessing a compound's ability to prevent the hind limb tonic extension component of the seizure in groups of mice induced by maximal electroshock (MES) after oral or intraperitoneal administration according to the procedures of the Epilepsy Branch, NINCDS as published by R. J. Porter, et al., Cleve. Clin. Quarterly 1984, 51, 293, and compared to the standard agents dilantin and phenobarbital. Activities ($ED_{50}$'s) in the range of 10–400 m/k after oral administration in this assay system were obtained.

Anti-epileptic properties of a compound may also be determined by measuring the effects of the compound on mouse central neurons in cell culture. Methods for assessing a compounds ability to inhibit sustained high frequency repetitive firing of sodium dependent action potentials are described by McLean et al, J. Pharmacol. Exp. Ther., 227, 779–789 (1983).

For the above-mentioned uses the dosage administered will, of course, vary with the compound employed, the mode of administration and the treatment desired. However, in general, satisfactory results are obtained when the compounds are administered at a daily dosage of from about 0.1 mg to about 20 mg per kg of animal body weight, preferably given in divided doses 1 to 4 times a day or in sustained release form. For man the total daily dose is in the range of from 5 mg to 1,400 mg more preferably from 10 mg to 500 mg, and unit dosage forms suitable for oral administration comprise from 2 mg to 1,400 mg of the compound admixed with a solid or liquid pharmaceutical carrier or diluent.

The compounds of formula I, and pharmaceutically acceptable acid addition salts thereof, may be used on their own or in the form of appropriate medicinal preparations for enteral or parenteral administration.

According to the invention, there is also provided a pharmaceutical composition comprising preferably less than 80% and more preferably less than 50% by weight of a compound of formula I, or a pharmaceutically acceptable salt thereof, in admixture with a pharmaceutically acceptable adjuvant, diluent or carrier.

Examples of such adjuvants, diluents and carriers are: for tablets and dragees: lactose, starch, talc, stearic acid; for capsules: tartaric acid or lactose; for injectable solutions: water, alcohols, glycerin, vegetable oils; for suppositories: natural or hardened oils or waxes.

Compositions in a form suitable for oral, i.e. oesophageal administration include tablets, capsules and dragees;

Sustained release compositions include those in which the active ingredient is bound to an ion exchange resin which is optionally coated with a diffusion barrier to modify the release properties of the resin.

We prefer the composition to contain up to 50% and more preferably up to 25% by weight of the compound of formula I, or of the pharmaceutically acceptable derivative thereof.

The compounds of formula I and pharmaceutically acceptable derivatives thereof have the advantage that they are less toxic, more efficacious, are longer acting, have a broader range of activity, are more potent, produce fewer side effects, are more easily absorbed or have other useful pharmacological properties, than compounds of similar structure.

The invention is illustrated, but in no way limited, by the following examples.

PREPARATION OF INTERMEDIATES

Intermediate 1

Preparation of 5,5-diphenyl-2-piperidinone
4-Carbethoxy-2,2-diphenylbutanenitrile To a stirred suspension of sodium hydride (27 g of a 60% oil suspension) in 600 mL of dry dimethylformamide at room temperature was added over 1 hour a solution of diphenyl acetonitrile (130 g, o.67 mol) in 400 mL of DMF. the mixture was stirred until the evolution of hydrogen ceased, about 1 hour. Ethyl 3-chloropropionate (90 mL, 1 mol) was added dropwise over 1 hour and the resulting mixture was stirred for a further 1 hour, then it was partitioned between water and ether. The organic layer was washed with brine and dried. Concentration of the solvents afforded a residue which was vacuum distilled to give 4-carbethoxy-2,2-diphenyl-butanenitrile (110 g).

5,5-Diphenyl-2-piperidinone

A mixture of the nitrile (50 g, 0.17 mol) and platinum oxide (2 g) in acetic acid (250 mL) was subjected to 40 psi of hydrogen on the Parr apparatus for 3 days. The catalyst was filtered and the filtrate concentrated to dryness using a toluene azeotrope. The resulting semi-solid residue was triturated with toluene and filtered to give the title product as a white solid (15 g), mp 177°–180° C.

Using essentially the same methods as described above and substituting ethyl 2-bromoacetate for ethyl 3-chloropropionate gave 4,4 diphenyl-2-pyrrolidinone.

Intermediate 2

Preparation of cis and trans-5,6-diphenyl-2-piperidinone
Ethyl-4,5-diphenyl-5-oxopentanoate To a solution of 140 g (0.71 mol) of deoxybenzoin and 170 g (1.7 mol) of ethyl acrylate in 2 L of absolute ethanol at ambient temperature was added in portions 20 mL of 50% aqueous sodium hydroxide. An additional 170 g (1.7 mol) of ethyl acrylate was then added over a 15 min. period. The mixture was stirred vigorously for 2.5 h, poured into 1 L of water and extracted with $3 \times 1$ L of ether. The organic layers were combined, washed with water and brine, and dried over sodium sulfate. The filtrate was concentrated to near dryness, triturated with 1.5 L of pentane, filtered and the filtrate allowed to stand at $-20°$ C. giving 145 g (69%) of ethyl 4,5-diphenyl-5-oxopentanoate as a white solid (top 45°–57° C.).

Ethyl 4,5-diphenyl-5-oximidopentanoate

A mixture of 145 g (0.49 mol) of ethyl-4,5-diphenyl-5-oxopentanoate, 40 g (0.58 mol) of hydroxylamine hydrochloride, and 142 g (1.8 mol) of pyridine in 300 mL of absolute ethanol was allowed to stand at ambient temperature for 3.5 days. The mixture was poured into 500 mL of water and extracted with $3 \times 700$ mL of ether. The organic layers were combined, washed with $3 \times 200$ mL of 1N hydrochloric acid, water, brine and dried over sodium sulfate. Concentration of the filtrate gave 150 g (98 %) of ethyl 4,5-diphenyl-5-oximidopentanoate as a white solid.

Cis- and trans-5,6-diphenyl-2-piperidinone

A mixture of 150 g (0.48 mol) of ethyl 4,5-diphenyl-5-oximidopentanoate and 20 g of 10% palladium on carbon in 1 L of glacial acetic acid was subjected to 40 psi of hydrogen on a Parr apparatus for 2 days. The catalyst was filtered and the filtrate concentrated to near dryness by azeotropic removal of the acetic acid with toluene. The resulting residue was dissolved in 2 L of ethyl acetate and washed successively with $3 \times 200$ mL of 1N hydrochloric acid, water, brine and dried over sodium sulfate. Repeated recrystallization of the crude solid product from toluene gave 35 g (29%) of pure trans-5,6-diphenyl-2-piperidinone as a white solid (mp 160°–164° C.). Concentration of the toluene filtrates and repeated recrystallization from toluene gave 35 g (29%) of pure cis-5,6-diphenyl-2-piperidinone as a white solid (mp 183°–186° C.). Any remaining mixture of cis and trans isomers could be separated by chromatography on silica gel. Workup of the aqueous acidic washes by standard basification and extraction procedures gave 40 g (28%) of ethyl 5-amino-4,5--diphenylpentanoate as a mixture of isomers, which could be warmed at 50°–60° C. in 150 mL of pyridine for 25 h to give, after an extractive workup procedure, an additional 30 g of a mixture of cis and trans isomers, separable by recrystallization or chromatography.

Intermediate 3

Preparation of 6,6-diphenyl2-piperidinone 4-bromo-1,1-diphenyl-1-butene

To a vigorously stirred solution of 250.g (1.1 mol) of cyclopropyl diphenyl carbinol in 2.5 liters of toluene at ambient temperature was added rapidly 3.1 liters of 48% aqueous hydrobromic acid. After stirring for several hours, the layers were separated, the organic phase was washed with 1 liter of water, 1 liter of 10% aqueous sodium bicarbonate, and dried over sodium sulfate. The resulting crude oil residue was subjected to high-vacuum short path distillation to give 300 .g (95%) of 4-bromo-1,1-diphenyl-l-butene as a clear oil.

5,5-diphenyl-4-pentenenitrile

To a stirred solution of 73.g (1.5 mol) of sodium cyanide in 1 liter of hexamethylphosphoramide at ambient temperature was added over a 1 hour period a solution of 290. g ( 1 mol) of 4-bromo-1,1-diphenyl-1-butene in 0.5 liters of hexamethylphosphoramide. The mixture was stirred overnight, poured into 2 liters of water and extracted with 3×1 liters of ether. The ether extracts were combined, washed with 3×0.5 liters of Water, 0.5 liters of brine, and dried over sodium sulfate. The resulting crude solid was recrystallized from isopropyl ether to give 190 .g (80%) of 5,5-diphenyl-4-pentenenitrile as a white solid (mp 64°-66° C.) .

6,6-diphenyl-2-piperidinone

A stirred mixture of 24. g (0.17 tool) of granular phosphorus pentoxide and 240.g (2.5 mol) of 98% methanesulfonic acid was maintained at 110 ° C. until all the solid dissolved ( 1 hour) . To this solution was added in portions over several minutes 12 g (0.05 mol) of 5,5-diphenyl-4-pentenenitrile. The resulting dark mixture was heated for 5 minutes longer and then carefully added to an ice-cooled vigorously stirred mixture of 1 liter of saturated aqueous sodium bicarbonate and 1 liter of ethyl acetate. The basic aqueous phase was extracted with 3×500 ml of fresh ethyl acetate, the organic layers were combined, washed with 2×500 ml of water, 1×500 ml brine, and dried over sodium sulfate. The resulting crude solid was recrystallized from toluene to give 8.5 g (66%) of 6,6-diphenyl-2-piperidinone as a white solid (mp 193°-196° C.) .

PREPARATION OF EXAMPLES

Example 1

Preparation of 1-(Aminomethyl)-5,5-diphenyl-2-piperidinone maleate a) 1-(hydroxymethyl)-5,5-diphenyl-2-piperidinone To a stirred mixture of 37 g (0.147 mol) of 5,5 diphenyl-2-piperidinone and 24 g of sodium hydroxide in 170 mL of ethanol at ambient temperature was added dropwise 165 mL of a 35-40% formaldehyde in water solution during 10 minutes. The mixture was heated at reflux temperature overnight, concentrated to near dryness and partitioned between ethyl acetate and water. The organic layer was washed with water and brine, and dried. Concentration at less than 30° C. under vacuum, trituration with hexanes and filtration gave 28 g of product, mp 140°-150° C.(decomp.).

b) 1-(Chloromethyl)-5,5-diphenyl-2-piperidinone

To a stirred suspension of 28 g (0.1 mol) of the product of step (a) in 150 mL of benzene at 10° C. was added dropwise a solution of 16 mL (1.63 mol) of thionyl chloride in 150 mL of benzene. The mixture was allowed to warm to ambient temperature, stirred overnight and concentrated to dryness. Fresh benzene was added and the solution reconcentrated several more times to give 27 g of crude 1-(chloromethyl)-5,5-diphenyl-2-piperidinone as a white solid.

c) 1-(aminomethyl)-5,5-diphenyl-2-piperidinone maleate

1-Chloromethyl-5,5-diphenyl-2-piperidinone (16g) was added portionwise over 15 min. to a mixture of ammonia (100 ml), toluene (100 ml) and THF (100 ml) at −40° C. with stirring and the mixture was allowed to warm to room temperature over 3 days. The reaction mixture was partitioned between water and chloroform and the combined organic solvents were washed with water and brine. Concentration of the solvents to dryness gave 15 g of crude product which was dissolved in absolute ethanol (150 ml) and treated with maleic acid (6 g) dissolved in ethanol (15 ml). Ether (50 ml) was added and the precipitated solid (13 g) was filtered off. The solid (13 g) was dissolved in 850 ml. of 40° C. water, filtered and the aqueous solution was freeze-dried to give the title product as a maleate salt (mp 136° C.).

Example 2

Trans-1-aminomethyl-5,6-diphenyl-2-piperidinone.

Using essentially the method described above in Example 1a and substituting trans-5,6-diphenyl-2-piperidinone for 5,5-diphenyl-2-piperidinone resulted in the formation of trans-1-(hydroxymethyl)-5,6-diphenyl-2-piperidinone (mp 127°-129 ° C.).

Using essentially the methods described in Example 1b and 1c above and substituting trans-1-(hydroxymethyl)-5,6-diphenyl--2-piperidinone for 1-(hydroxymethyl)-5,5-diphenyl--2--piperidinone, gave trans-1-(aminomethyl)-5,6---diphenyl-2-piperidinone Example 3

1-[(Methylamino)methyl]-5,5-diphenyl-2-piperidinone hydrochloride 1-(Chloromethyl)-5,5-diphenyl-2-piperidinone (27 g) was added portionwise during 20 min. to a solution of methylamine (120ml) in a mixture of toluene (100 ml) and THF (100 ml) at −30° C. with stirring and the mixture was allowed to warm to room temperature overnight. The reaction mixture was partitioned between ethyl acetate and water and the organic solvent layer was washed with water and brine. The aqueous layers were re-extracted with ethyl acetate and then chloroform. All the organic extracts were combined and concentrated to give the crude title product as a solid which was converted to the hydrochloride salt by dissolution in isopropanol:methanol(5:1) and then adding portionwise a solution of hydrogen chloride in isopropanol until the medium was acidic. The solution was cooled overnight at 0°-5° C. and the hydrochloride salt of the title product was filtered of as a solid, mp 169°-171° C.

Example 4

Following essentially the methods of Example 3 and substituting ethylamine, isopropylamine, cyclopropylamine, propylamine or dimethylamine for methylamine resulted in the formation of the following compounds:
a) 1-[(ethylamino)methyl]-5,5-diphenyl-2-piperidinone hydrochloride, mp 100°-105° C.,
b) 1-[(isopropylamino)methyl]-5,5-diphenyl-piperidinone hydrochloride, mp 170°-172° C.,
c) 1-[(cyclopropylamino)methyl]-5,5-diphenyl-2-piperidinone hydrochloride, mp 143°-145° C., d) 1-[(propylamino)methyl]-5,5-diphenyl-2-piperidinone maleate, mp 161°-164° C., and
e) 1-[(dimethylamino)methyl]-5,5-diphenyl-2-piperidinone hydrochloride, mp 100°-110° C. dec..

Example 5

1-[3-(Dimethylamino)propyl]-5,5-diphenyl-2-piperidinone hydrochloride

To a vigorously stirred mixture of 5,5-diphenyl 2-piperidinone (5.0 g) and 45% potassium hydroxide (15 ml) in dimethyl sulfoxide (50 ml) was added in one portion 3-(dimethylamino)propyl chloride (5.5g) at room temperature. The reaction was stirred overnight, then it was partitioned between water and ethyl acetate. The organic layer was separated, washed with water and dried. Evaporation of the solvents afforded a syrup which was chromatographed over ammonia-washed silica gel and the resultant title product amine was treated with isopropanol/HCl. The precipitated .hydrochloride salt was collected by filtration, recrystallized from absolute ethanol and dried to give the title product as the hydrochloride salt (3.6 g), mp 220°-5° C.

Example 6

1-[2-(Dimethylamino)ethyl]-5,5-diphenyl-2-piperidinone hydrochloride

Following essentially the method of Example 5 and substituting 2- (dimethylamino) ethyl chloride for 3-(dimethylamino) propyl chloride resulted in the formation of 1-[2-(dimethylamino)ethyl]-5,5-diphenyl-2-piperidinone hydrochloride, mp 247°-248 ° C.

Example 7

1- (Aminomethyl) -4,4,diphenyl-2-pyrrolidinone maleate

Using essentially the method described above in Example 1, steps a, b and c, and substituting 4,4- diphenyl-2-pyrrolidinone for 5,5-diphenyl-2-piperidinone, gave 1-(aminomethyl)-4,4-diphenyl-2-pyrrolidinone maleate, mp 141°-143° C.

Example 8

1-(Aminomethyl)-5,5-diphenyl-2-piperdinone maleate monohydrate

Using essentially the methods described in Example 1, the solid maleate obtained by precipitation from ethanol with ether was obtained and found to contain 12% ethanol, wt=24.8 g. The solid was dissolved in water (100 mL) at 60° C. On cooling to 15° C., a crystalline solid precipitated and was filtered off to give the title compound in the form of a monohydrate, wt=21.5 g, mp=95°-105° C.

What we claim is:

1. A compound of formula I

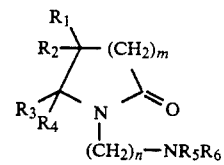

wherein $R_1$ and $R_2$ independently represent phenyl or phenyl substituted by one or more groups selected from halogen, hydroxyl, nitro, amino, $C_{1-6}$ alkyl and $C_{1-6}$ alkoxy;

$R_3$ and $R_4$ independently represent hydrogen or $C_1-C_6$ alkyl;

$R_5$ and $R_6$ independently represent hydrogen, $C_{1-6}$ alkyl or $C_{3-6}$ cycloalkyl, or $R_5$ and $R_6$ together with the nitrogen form a $C_{4-6}N$ heterocycle;

m represents an integer from 1-2; and n represents an integer from 1-3;

or a pharmaceutically acceptable acid addition salt thereof.

2. The compound of claim 1 wherein both $R_1$ and $R_2$ are phenyl.

3. The compound of claim 1 wherein $R_1$ and $R_2$ are phenyl and $R_3$ and $R_4$ may be the same or different and are hydrogen or $C_{1-6}$ alkyl.

4. The compound of claim 1 selected from the group consisting of

1-[(methylamino)methyl]-5,5-diphenyl-2-piperidinone;
1-(aminomethyl)-5,5-diphenyl-2-piperidinone;
1-[(dimethylamino)methyl]-5,5-diphenyl-2-piperidinone;
1-[ethylamino)methyl -5,5-diphenyl-2-piperidinone;
1-[isopropylamino)methyl -5,5-diphenyl-2-piperidinone;
1[cyclopropylamino)methyl]-5,5-diphenyl-2-piperidinone;
1-[(propylamino)methyl]-5,5-diphenyl-2-piperidinone;
1-[3-(dimethylamino)propyl]-5,5-diphenyl-2-piperidinone;
1-[2-(dimethylamino)ethyl]-5,5-diphenyl-2-piperidinone;
1-(aminomethyl)-4,4-diphenyl-2-pyrrolidinone;
or a pharmaceutically acceptable acid addition salt thereof.

* * * * *

UNITED STATES PATENT AND TRADEMARK OFFICE
CERTIFICATE OF CORRECTION

PATENT NO. : 5,334,720
DATED : August 2, 1994
INVENTOR(S) : Richard J. SCHMIESING, et al It is certified that error appears in the above-indentified patent and that said Letters Patent is hereby corrected as shown below:

Column 10,

Claim 4, lines 39 and 40 change " 1-[isopropylamino)methyl -5,5-diphenyl-2-piperidinone; "

to --1-[(isopropylamino)methyl]-5,5-diphenyl-2-piperidinone;

Signed and Sealed this

Eighth Day of October, 1996

Attest:

BRUCE LEHMAN

Attesting Officer     Commissioner of Patents and Trademarks